United States Patent
Gross et al.

(10) Patent No.: US 6,667,322 B2
(45) Date of Patent: *Dec. 23, 2003

(54) ANTIDEPRESSANT CHROMAN AND CHROMENE DERIVATIVES OF 3-(1,2,3,6-TETRAHYDRO-4-PYRIDINYL)-1H-INDOLE

(75) Inventors: Jonathan Laird Gross, Robbinsville, NJ (US); Richard Eric Mewshaw, King of Prussia, PA (US); Gary Paul Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/264,376

(22) Filed: Oct. 4, 2002

(65) Prior Publication Data

US 2003/0100579 A1 May 29, 2003

Related U.S. Application Data

(60) Provisional application No. 60/328,120, filed on Oct. 9, 2001, provisional application No. 60/327,417, filed on Oct. 5, 2001, and provisional application No. 60/327,400, filed on Oct. 5, 2001.

(51) Int. Cl.$^7$ .................. A61K 31/4439; C07D 401/04
(52) U.S. Cl. .................. 514/338; 514/321; 514/300; 546/277.4; 546/197; 546/113
(58) Field of Search .............. 546/277.4, 197, 546/113; 514/338, 321, 300

(56) References Cited

U.S. PATENT DOCUMENTS

| | | | |
|---|---|---|---|
| 5,371,094 A | 12/1994 | Heine et al. | |
| 5,468,767 A | 11/1995 | Cipollina et al. | |
| 5,741,789 A | 4/1998 | Hibschman et al. | |
| 5,750,724 A | 5/1998 | Kang et al. | |
| 5,869,490 A | 2/1999 | Stack | |
| 6,458,802 B1 * | 10/2002 | Tran et al. | 514/291 |

FOREIGN PATENT DOCUMENTS

| | | |
|---|---|---|
| WO | WO 95/07274 | 3/1995 |
| WO | WO 98/40386 | 9/1998 |

OTHER PUBLICATIONS

CA 137:337896, Husbands et al. 2002.*

* cited by examiner

*Primary Examiner*—Jane Fan
(74) *Attorney, Agent, or Firm*—Woodcock Washburn LLP

(57) ABSTRACT

Compounds of the formula

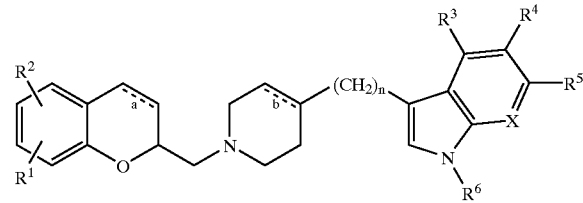

useful for the treatment of depression and other diseases such as obsessive compulsive disorder, panic attacks, generalized anxiety disorder, social anxiety disorder, sexual dysfunction, eating disorders, obesity, addictive disorders caused by ethanol or cocaine abuse and related illnesses.

27 Claims, No Drawings

ANTIDEPRESSANT CHROMAN AND CHROMENE DERIVATIVES OF 3-(1,2,3,6-TETRAHYDRO-4-PYRIDINYL)-1H-INDOLE

BACKGROUND OF THE INVENTION

This application claims priority from copending provisional applications Serial No. 60/328,120, filed Oct. 9, 2001, Serial No. 60/327,417, filed Oct. 5, 2001, and No. 60/327,400, filed Oct. 5, 2001, the entire disclosures of which are hereby incorporated by reference.

Major depressive disorder affects an estimated 340 million people worldwide. According to the World Health Organization, depression is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also results in more than $40 billion in annual costs in the United States alone, due to premature death, lost productivity, and absenteeism.

Selective serotonin reuptake inhibitors (SSRIs) have had significant success in treating depression and related illnesses and have become among the most prescribed drugs. They nonetheless have a slow onset of action, often taking several weeks to produce their full therapeutic effect. Furthermore, they are effective in fewer than two-thirds of patients.

SSRIs work by blocking the neuronal reuptake of serotonin, which tends to increase the concentration of serotonin in the synaptic space, and thus increase the activation of postsynaptic serotonin receptors. However, although a single dose of an SSRI can inhibit the neuronal serotonin transporter and thus would be expected to increase synaptic serotonin, long-term treatment is required before clinical improvement is achieved. It has been suggested that the SSRIs increase the serotonin levels in the vicinity of the serotonergic cell bodies and that the excess serotonin activates somatodendritic autoreceptors, 5-HT$_{1A}$ receptors, causing a decrease in serotonin release in major forebrain areas. This negative feedback limits the increment of synaptic serotonin that can be induced by antidepressants acutely. Over time, the somatodendritic autoreceptors become desensitized, allowing the full effect of the SSRI to be expressed in the forebrain. This time period corresponds to the latency for the onset of antidepressant activity [Perez, V., et al., *The Lancet,* 349:1594–1597 (1997)].

A 5-HT$_{1A}$ agonist or partial agonist acts directly on postsynaptic serotonin receptors to increase serotonergic neurotransmission during the latency period for the SSRI effect. Accordingly, the 5-HT$_{1A}$ partial agonists buspirone and gepirone [Feiger, A., *Psychopharmacol. Bull.,* 32(4), 659–665 (1996), Wilcox, C., *Psychopharmacol. Bull.,* 32(3), 335–342 (1996)] and the 5-HT$_{1A}$ agonist flesinoxan [Grof, P., *International clinical Psychopharmacology,* 8(3), 167–72 (1993)] have shown efficacy in clinical trials for the treatment of depression. Furthermore, such agents would also stimulate the somatodendritic autoreceptors, thus hastening their desensitization and decreasing the SSRI latency period. An agent with a dual mechanism of antidepressant action would be expected to have greater efficacy and thus reduce the number of patients refractory to treatment. Indeed, buspirone augmentation has been shown to produce marked clinical improvement in patients initally unresponsive to standard antidepressant therapy [Dimitriou, E., *J. Clinical Psychopharmacol.,* 18(6), 465–469 (1998)].

Thus, it is highly desirable to provide improved compounds which both inhibit serotonin reuptake and which are agonists or partial agonists of the 5-HT$_{1A}$ receptor.

DESCRIPTION OF THE INVENTION

In accordance with this invention, there is provided a group of novel compounds of the formula:

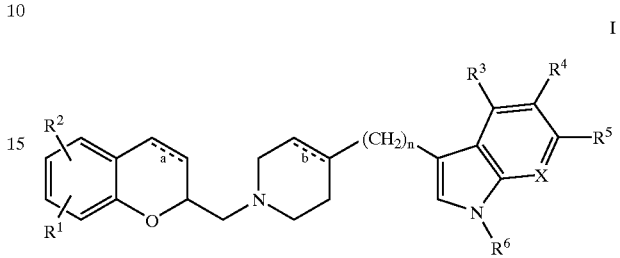

I wherein $R^1$ and $R^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halo, cyano, carboxamido, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

the dotted lines at a and b independently represent optional double bonds; and n is an integer 0, 1 or 2;

or a pharmaceutically acceptable salt thereof.

In some preferred embodiments of the invention $R^1$ and $R^2$ are independently hydrogen, halo, cyano, carboxamido, trifluoromethyl, amino, alkyl of one to six carbon atoms or alkoxy of one to six carbon atoms. More preferably, one of $R^1$ and $R^2$ is alkoxy of 1 to 6 carbon atoms or together $R^1$ and $R^2$ form methylenedioxy, ethylenedioxy or propylenedioxy. One of $R^1$ and $R^2$ is still more preferably alkoxy of 1 to 3 carbon atoms.

In some preferred embodiments of the invention $R^3$, $R^4$ and $R^5$ are independently selected from hydrogen, halo, cyano, alkyl of one to six carbon atoms, and alkoxy of one to six carbon atoms. Still more preferably $R^3$, $R^4$ and $R^5$ are independently selected from hydrogen, halogen and cyano.

$R^6$ is preferably hydrogen or lower alkyl.

X is preferably $CR^7$. When X is $CR^7$, then $R^7$ is preferably hydrogen, halo, cyano, alkyl of one to six carbon atoms, or alkoxy of one to six carbon atoms and more preferably hydrogen, halogen or cyano.

Of the compounds of Formula I, some preferred members are those in which $R^1$ and $R^2$ are, independently, hydrogen, halo, cyano, carboxamido, trifluoromethyl, amino, alkyl of one to six carbon atoms or alkoxy of one to six carbon atoms; $R^3$, $R^4$, $R^5$ and $R^7$ are independently selected from hydrogen, halo, cyano, alkyl of one to six carbon atoms, or alkoxy of one to six carbon atoms; n is an integer 0 or 1; and $R^6$, X and the dotted line are defined as above.

More preferred compounds are those of Formula I in which $R^1$ is alkoxy of one to six carbon atoms and is attached to position 8 of a chroman moiety, $R^2$ and $R^6$ are hydrogen, $R^3$, $R^4$, $R^5$ and $R^7$ are independently selected from hydrogen, halo or cyano, X is $CR^7$, n is 0 and the dotted line in the azaheterocycle represents a double bond.

This invention relates to both the R and S stereoisomers of the 2-aminomethyl-chromans and chromenes, as well as to mixtures of the R and S stereoisomers. Throughout this application, the name of the product of this invention, where the absolute configuration of the 2-aminomethyl-chromans and chromenes is not indicated, is intended to embrace the individual R and S enantiomers as well as mixtures of the two.

In some embodiments of the present invention the R stereoisomer is preferred.

Where a stereoisomer is preferred, it may in some embodiments be provided substantially free of the corresponding enantiomer. Thus, an enantiomer substantially free of the corresponding enantiomer refers to a compound which is isolated or separated via separation techniques or prepared free of the corresonding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared as described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention include:
2-{[1-(3,4-dihydro-2H-chromen-2-ylmethyl)-4-piperidinyl]methyl}-5-fluoro-1H-indole;
3-[1-(3,4-dihydro-2H-chromen-2-ylmethyl)-1,2,3,6-tetrahydro-4-pyridinyl]-1H-indole;
3-[1-(3,4-dihydro-2H-chromen-2-ylmethyl)-1,2,3,6-tetrahydro-4-pyridinyl]-5-fluoro-1H-indole;
5-fluoro-3-(1-{[8-methoxy-3,4-dihydro-2H-chromen-2-yl]methyl}-1,2,3,6-tetrahydro-4-pyridinyl)-1H-indole;
(3-(1-{[8-methoxy-3,4-dihydro-2H-chromen-2-yl]methyl}-1,2,3,6-tetrahydro-4-pyridinyl)-1H-indole;
3-[1-(3,4-dihydro-2H-chromen-2-ylmethyl)-1,2,3,6-tetrahydro-4-pyridinyl]-6-fluoro-1H-indole;
6-fluoro-3-(1-{[8-methoxy-3,4-dihydro-2H-chromen-2-yl]methyl}-1,2,3,6-tetrahydro-4-pyridinyl)-1H-indole;
5-fluoro-3-(1-{[8-methoxy-2H-chromen-2-yl]methyl}-1,2,3,6-tetrahydro-4-pyridinyl)-1H-indole; and
3-(1-{[8-methoxy-2H-chromen-2-yl]methyl}-1,2,3,6-tetrahydro-4-pyridinyl)-1H-indole; and pharmaceutical salts thereof.

The compounds of the invention are prepared by conventional methods. Unless otherwise noted, the variables used in the following schemes are as defined above. Specifically, the appropriate azaheterocycle (2) is combined with a suitably substituted chroman or chromene methyltosylate or halide (1) in a solvent such as dimethyl sulfoxide and heated to a temperature of 70–100° C. for several hours as illustrated in Scheme I below. Alternatively, the azaheterocycle may be acylated with a suitably substituted chroman or chromene carboxylic acid chloride, and the resulting amide reduced to the amine with an appropriate reducing agent such as lithium aluminum hydride or borane/THF. The azaheterocycle may

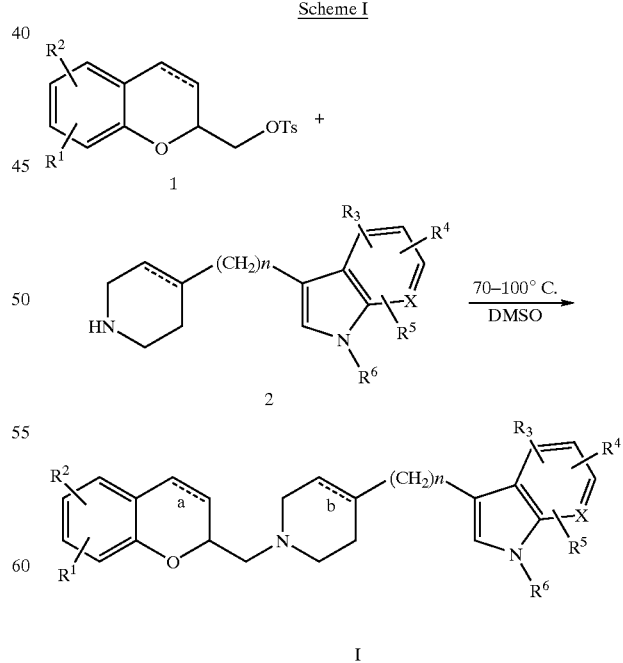

Scheme I also be combined with a suitably substituted chroman or chromene carboxaldehyde in the presence of a reducing agent such as sodium cyanoborohydride. The compounds of the invention may be resolved into their enantiomers by conventional methods.

The azaheterocycles required to prepare the compounds of the invention are known compounds. The chroman methyltosylates or halides are known compounds or they can be prepared stereoselectively by the procedure illustrated in Scheme II below. The appropriately substituted salicylaldehyde (3) is first protected with a suitable protecting group, such as benzyl, and then the aldehyde (4) is reduced to the alcohol by treatment with a reducing agent such as sodium borohydride. The resulting alcohol is converted to the bromide (5) by treatment with triphenylphosphine and carbon tetrabromide and the product coupled with allyl magnesium bromide to afford the homoallyl derivative (6). The terminal olefin can be stereoselectively converted to the vicinal diol (7) by treatment with the requisite, commercially available Sharpless Asymmetric Dihydroxylation reagent, AD-mix-α or β, to provide either the (R)- or (S)-enantiomer respectively, of the diol as the major product. Deprotection of the phenol with hydrogen and palladium on carbon followed by conversion of the diol to the bromoacetate with HBr in acetic acid provides (8). Stereospecific cyclization to the optically active chroman-2-methanol (10) is effected by mild treatment with base.

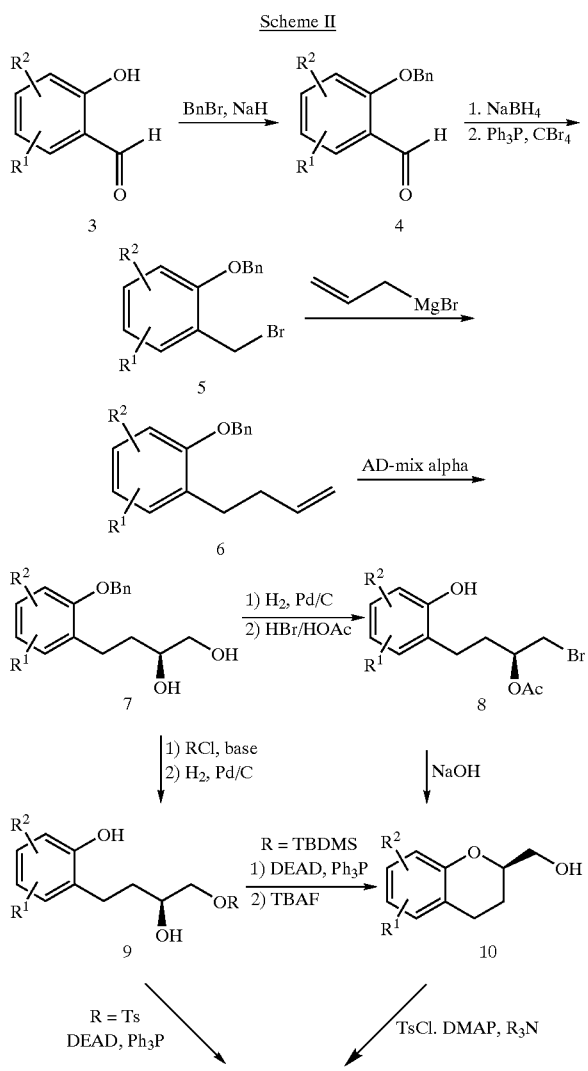

Treatment with p-toluenesulfonyl chloride in the presence of a tertiary amine base and catalytic 4-(dimethylamino) pyridine (DMAP) provides the chroman methyltosylate (11) suitable for preparation of the chroman derivatives claimed in this invention. Alternatively, formation of the chroman may be effected by either selective protection of the primary alcohol with a suitable protecting group such as a silyl ether, or via chemoselective tosylation of the primary alcohol with one equivalent of tosyl chloride followed by cyclization under Mitsunobu conditions.

The chroman and chromene methyltosylates may alternatively be prepared stereospecifically by the following procedure of Scheme III. The appropriately substituted ortho-hydroxystyrene (13) may be prepared from a phenol via allylation or from a salicylaldehyde via a Wittig olefination. Olefination may be accomplished by treatment with the ylide derived from methyltriphenylphoshonium bromide and butyllithium. Mitsunobu reaction of the phenol with 3-butene-1,2-diol, suitably functionalized at the primary alcohol (where R is an O-protecting group or a suitable leaving group), in the presence of triphenylphoshine and diethylazodicarboxylate provides the diene substrate for the Ring Closing Metathesis (RCM) polymerization reaction. The Mitsunobu reaction proceeds with a net inversion of configuration at the stereogenic center containing the secondary alcohol. The use of a chiral non-racemic alcohol allows for reliable incorporation of stereochemical information. Cyclization of the diene occurs in the presence of bis(tricyclopentylphosphine)benzylidine ruthenium (IV) dichloride to give the chromene (14) in optically pure form. Reduction of the double bond is accomplished via hydrogenation in ethanol in the presence of a palladium catalyst to give the 2-hydroxymethyl-chroman (11).

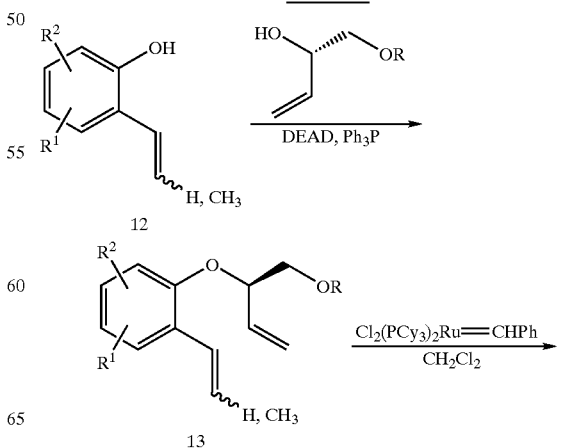

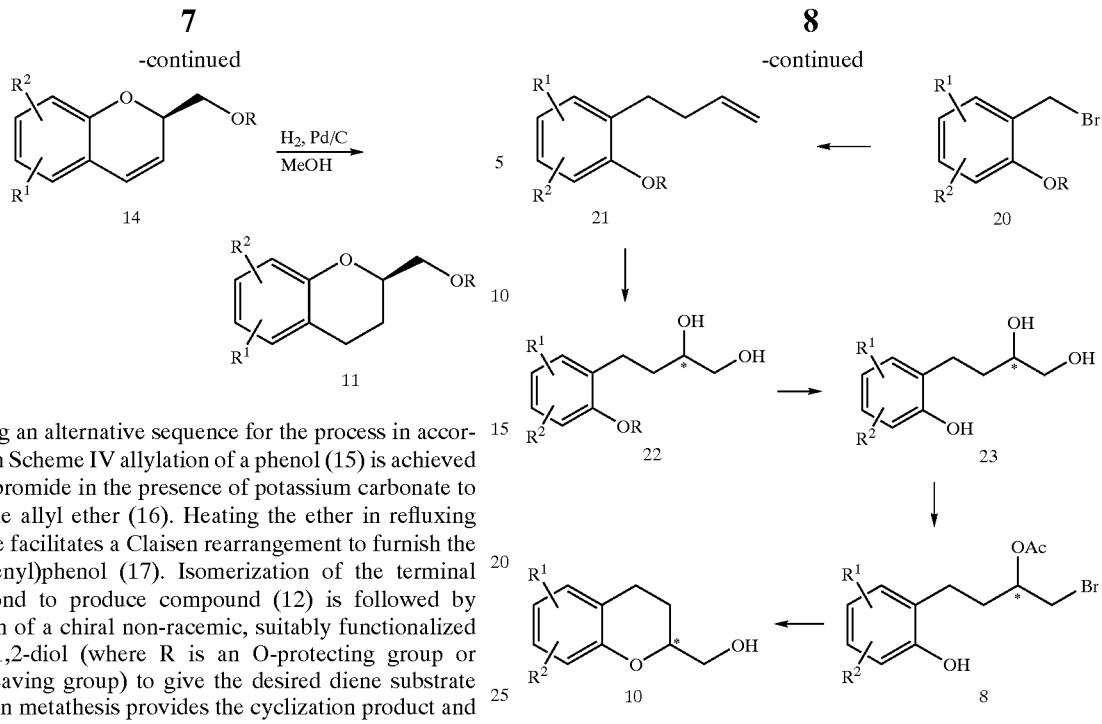

Utilizing an alternative sequence for the process in accordance with Scheme IV allylation of a phenol (15) is achieved with allylbromide in the presence of potassium carbonate to provide the allyl ether (16). Heating the ether in refluxing mesitylene facilitates a Claisen rearrangement to furnish the 2-(3-propenyl)phenol (17). Isomerization of the terminal double bond to produce compound (12) is followed by installation of a chiral non-racemic, suitably functionalized 3-butene-1,2-diol (where R is an O-protecting group or suitable leaving group) to give the desired diene substrate (13). Olefin metathesis provides the cyclization product and subsequent hydrogenation delivers a 2-hydroxymethyl-chroman.

Scheme IV

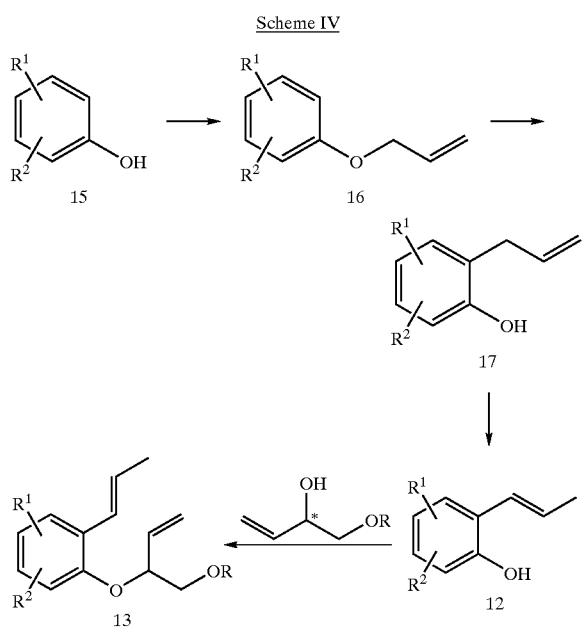

2-aminomethyl- and 2-azaheterocycimethyl-chromans may be stereoselectively prepared in accordance with the general guidance of the following Schemes.

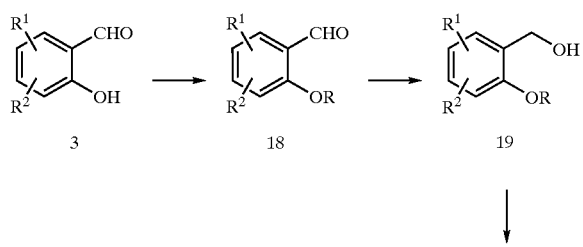

Thus, protection of the salicylaldehyde (3) as the corresponding benzyl ether is accomplished via treatment with benzyl bromide in the presence of potassium carbonate (SCHEME V). Reduction of the benzaldehyde (18) (where R is hydrogen, an O-protecting group or a suitable leaving group) with sodium borohydride provides the benzyl alcohol (19) which is converted to the benzylbromide (20) by treatment with carbon tetrabromide and triphenylphoshine. Addition of allyl magnesium bromide to the bromide furnishes the butenyl group of compound (21) as the substrate for the dihydroxylation step. Introduction of a vicinal diol in a non-racemic fashion is accomplished utilizing the Sharpless Asymmetric Dihydroxylation to produce (22). This reaction permits the introduction of the stereogenic center in a predictable, non-racemic fashion with the requisite disposition for further elaboration.

Removal of the benzyl ether is accomplished by hydrogenolysis with 10 wt. % palladium on activated carbon. Treatment of the resultant triol (23) with 30% HBr in acetic acid provides a regioisomeric mixture of acetoxy bromides (8) favoring the formation of the primary bromide as indicated. Cyclization with aqueous sodium hydroxide in methanol at 0° C. gives the 2-hydroxymethyl-chroman (10) as a mixture of enantiomers in a stereospecific fashion reflecting the original stereoselectivity of the dihydroxylation.

SCHEME VI

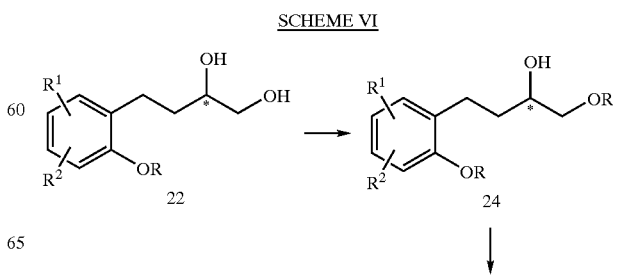

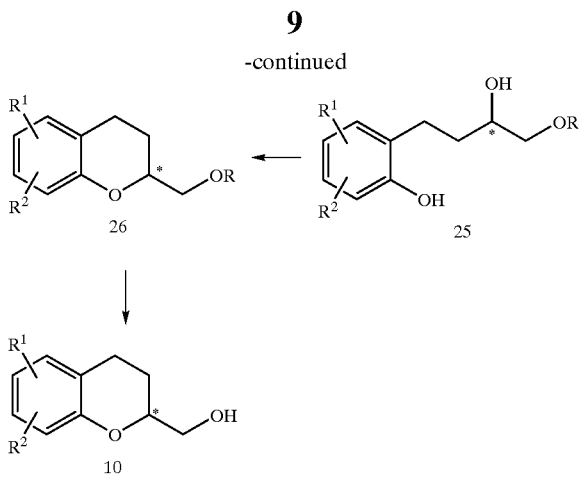

In accordance with Scheme VI, the 2-hydroxymethyl-chroman system may be prepared via chemoselective protection from the vicinal diol with an appropriate O-protecting group [suitable O-protecting groups can be found in T. W. Green and P. G. M. Wuts: Protective Groups in Organic Synthesis, Second Edition (Wiley, N.Y., (1991), "R"]. Hydrogenolysis of the benzyl ether (24) with 10 wt. % palladium on activated carbon affords the corresponding phenol (25) which is then subjected to cyclization using the Mitsunobu conditions as previously described to provide the protected 2-hydroxymethyl-chroman. Removal of the protecting group previously defined using the appropriate conditions then provides the 2-hydroxymethyl-chroman (10).

Scheme VII

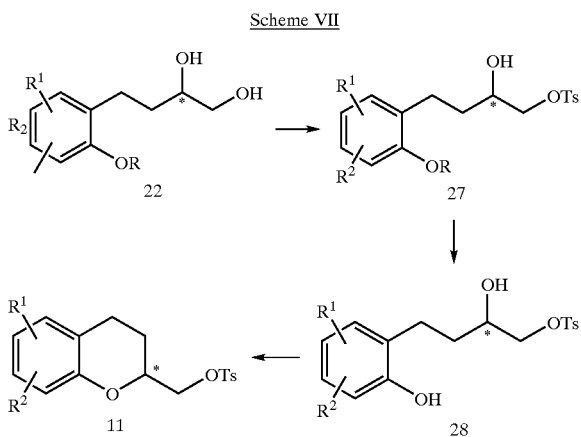

Additionally, the diol can be mono-tosylated by treatment with p-toluenesulfonyl chloride in pyridine (SCHEME VII). Deprotection of the benzyl ether followed by cyclization under Mitsunobu conditions as previously described affords the 3,4-dihydro-chromen-2-ylmethyl 4-methylbenzenesulfonate directly.

Like the antidepressants fluoxetine, paroxetine and sertraline, the compounds of this invention have the ability to potently block the reuptake of the brain neurotransmitter serotonin. They are thus useful for the treatment of depression and other diseases commonly treated by the administration of serotonin selective reuptake inhibitor (SSRI) antidepressants, such as obsessive compulsive disorder, panic attacks, generalized anxiety disorder, social anxiety disorder, sexual dysfunction, eating disorders, obesity, addictive disorders caused by ethanol or cocaine abuse and related illnesses. Moreover, the compounds of this invention have affinity for and agonists or partial agonist activity at brain 5-$HT_{1A}$ serotonin receptors. The 5-$HT_{1A}$ partial agonists buspirone and gepirone have demonstrated anxiolytic and antidepressant properties in clinical trials and the 5-$HT_{1A}$ full agonists flesinoxan has been shown to be an effective antidepressant. The compounds of the invention are thus exceedingly interesting and useful for treating depressive illnesses.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-$HT_{1A}$ receptor was established by testing the claimed compound's ability to displace [$^3$H] 8-OHDPAT (dipropylamino-tetralin) from the 5-$HT_{1A}$ serotonin receptor following a modification of the procedure of Hall et al., J. Neurochem. 44, 1685 (1985) which utilizes CHO cells stably transfected with human 5-$HT_{1A}$ receptors. The 5-$HT_{1A}$ affinities for the compounds of the invention are reported below as $K_i$'s.

Agonist activity at 5-$HT_{1A}$ receptors was established by using a $^{35}$S-GTPγbinding assay similar to that used by Lazareno and Birdsall (Br. J. Pharmacol. 109: 1120, 1993), in which the test compound's ability to affect the binding of $^{35}$S-GTPγS to membranes containing cloned human 5-$HT_{1A}$ receptors was determined. Agonists produce an increase in binding whereas antagonists produce no increase but rather reverse the effects of the standard agonist 8-OHDPAT. The test compound's maximum stimulatory effect is represented as the $E_{max}$, while its potency is defined by the $EC_{50}$.

The results of the three standard experimental test procedures described in the preceding three paragraphs were as follows:

| Compound | 5-HT Transporter Affinity KI (nM) | 5-$HT_{1A}$ Receptor Affinity KI (nM) | 5-HT1A Function $EC_{50}$ (nM) ($E_{max}$) |
|---|---|---|---|
| Example 1 | 0.13 | 265.0 | |
| Example 2 | 1.18 | 280.8 | (50) |
| Example 3 | 4.84 | 299.0 | 398.0 (83.0) |
| Example 4 | 9.50 | 34.36 | 283.0 (92.0) |
| Example 5 | 10.00 | 39.0 | 189.0 (79.0) |
| Example 6 | 0.34 | | 2483.0 (100) |
| Example 7 | 8.50 | 45.0 | 854.0 (64.0) |
| Example 8 | 20.0 | 142.7 | 1709.0 (60.0) |
| Example 9 | 9.50 | 96.48 | 208.0 (67.0) |

Hence the compounds of this invention are combined serotonin reuptake inhibitors/5$HT_{1A}$ agonists and are useful for the treatment of depression and other conditions related to or affected by the reuptake of serotonin and by the serotonin 1A receptor such as, depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addition, sexual dysfunction (including premature ejaculation), and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

EXAMPLE 1

2-{[1-(3,4-Dihydro-2H-chromen-2-ylmethyl)-4-piperidinyl]methyl}-5-fluoro-1H-indole To a solution of 3,4-dihydro-2H-chromen-2-ylmethyl 4-methylbenzenesulfonate (0.70 g, 2.19 mmol) in methyl sulfoxide (20 mL) was added 5-fluoro-2-(4-piperidinylmethyl)-1H-indole (0.51 g, 2.19 mmol) and triethylamine (0.25 g, 2.30 mmol) and the reaction mixture was heated to 90° C. for 8 h. The reaction mixture was allowed to cool to room temperature and was diluted with dichloromethane (200 mL), washed with water (2×100 mL), aqueous sodium chloride (100 mL), dried (magnesium sulfate) and the solvent was removed in vacuo to give a crude solid. Purification by flash column chromatography (silica, methanol:dichloromethane 1:19) provided a colorless oil which was dissolved in ethyl alcohol (5 mL) and treated with a solution of oxalic acid dihydrate (0.244 g, 1.94 mmol) in ethyl alcohol (10 mL). The resulting solid was filtered, washed (hexanes), and dried to give 0.370 g (44%)

of 2-{[1-(3,4-dihydro-2H-chromen-2-ylmethyl)-4-piperidinyl]methyl}-5-fluoro-1H-indole as a white solid. mp 187–190° C.; Anal. Calcd. for $C_{24}H_{27}FN_2O$.0.5 $C_2O_4H_2$.0.5$H_2O$: C, 69.43; H, 6.76; N, 6.48. Found: C, 69.23; H, 6.83; N, 6.48.

EXAMPLE 2

3-[1-(3,4-Dihydro-2H-chromen-2-ylmethyl)-1,2,3,6-tetrahydro-4-pyridinyl]-1H-indole To a solution of 3,4-dihydro-2H-chromen-2-ylmethyl 4-methylbenzenesulfonate (0.311 g, 0.98 mmol) in methyl sulfoxide (20 mL) was added 3-(1,2,3,6-tetrahydro-4-pyridinyl)-1H-indole (0.500 g, 2.52 mmol) and triethylamine (0.318 g, 3.14 mmol) and the reaction mixture was heated to 80° C. for 3 h. The reaction mixture was allowed to cool to room temperature and was diluted with ethyl acetate (200 mL), washed with water (3×100 mL), aqueous sodium chloride (100 mL), dried (magnesium sulfate) and the solvent was removed in vacuo to give a crude solid. Purification by flash column chromatography (silica, methanol:dichloromethane 1:19) provided 0.180 g (58%) of 3-[1-(3,4-dihydro-2H-chromen-2-ylmethyl)-1,2,3,6-tetrahydro-4-pyridinyl]-1H-indole as a pale yellow solid. mp 171–173° C.; Anal. Calcd. for $C_{23}H_{24}N_2O$: C, 80.20; H, 7.02; N, 8.13. Found: C, 79.97; H, 7.02; N, 8.14.

EXAMPLE 3

3-[1-(3,4-Dihydro-2H-chromen-2-ylmethyl)-1,2,3,6-tetrahydro-4-pyridinyl]-5-fluoro-1H-indole To a solution of 3,4-dihydro-2H-chromen-2-ylmethyl 4-methylbenzenesulfonate (0.500 g, 1.57 mmol) was added 5-fluoro-3-(1,2,3,6-tetrahydro-4-pyridinyl)-1H-indole (0.590 g, 2.73 mmol) and triethylamine (0.314 g, 3.10 mmol) and the reaction mixture was heated to 80° C. for 8 h. The reaction mixture was allowed to cool to room temperature and was diluted with ethyl acetate (200 mL), washed with water (3×100 mL), aqueous sodium chloride (100 mL), dried (magnesium sulfate) and the solvent was removed in vacuo to give a crude solid. Purification by flash column chromatography (silica, methanol:dichloromethane 1:9) provided 0.234 g (40%) of 3-[1-(3,4-dihydro-2H-chromen-2-ylmethyl)-1,2,3,6-tetrahydro-4-pyridinyl]-5-fluoro-1H-indole as a yellow solid. mp 172–175° C.; Anal. Calcd. for $C_{23}H_{23}FN_2O$: C, 76.22; H, 6.40; N, 7.73. Found: C, 75.82; H, 6.37; N, 7.63.

Intermediate 1

2-(Benzyloxy)-1-(3-butenyl)-3-methoxybenzene

To a solution of [2-(benzyloxy)-3-methoxyphenyl]methanol (14.82 g, 60.7 mmol) in dichloromethane (500 mL) at 0° C. was added carbon tetrabromide (26.16 g, 78.9 mmol) followed by portionwise addition of triphenyl phosphine (19.09 g, 72.8 mmol) and the reaction mixture was allowed to stir for 15 min. The reaction was quenched by the addition of water (500 mL) and extracted with dichloromethane (400 mL). The combined organic layers were washed with water (400 mL), aqueous sodium chloride (500 mL), dried (magnesium sulfate) and the solvent was removed in vacuo to give a crude solid. Purification by flash column chromatography (silica, ethyl acetate:hexanes 1:9) gave 18.46 g of a colorless oil which was dissolved in tetrahydrofuran (500 mL). The solution was cooled to 0° C. and allyl magnesiumbromide (1.0 M in diethyl ether, 121.4 mL, 121.4 mmol) was added dropwise and the reaction mixture was allowed to stir for 12 h at room temperature. The reaction was quenched by the addition of aqueous ammonium chloride (200 mL) and water (300 mL) and extracted with diethyl ether (3×250 mL). The combined organic layers extracts were washed with water (400 mL), aqueous sodium chloride (500 mL), dried (magnesium sulfate) and the solvent was removed in vacuo to give an oil. Purification by flash column chromatography (silica, ethyl acetate:hexanes 1:20) gave 13.84 g (85%) of 2-(benzyloxy)-1-(3-butenyl)-3-methoxybenzene as a colorless oil. $R_f$=0.62 (silica, ethyl acetate:hexanes 3:2); Anal. Calcd. for $C_{18}H_{20}O_2$.0.25 $H_2O$: C, 79.23; H, 7.57. Found: C, 79.02; H, 7.47.

Intermediate 2

4-[2-(Benzyloxy)-3-methoxyphenyl]-1,2-butanediol

To a suspension of AD-mix-α (63.28 g) in water:tert-butyl alcohol (1:1, 300 mL) cooled to 0° C. was slowly added via an addition funnel to a solution of 2-(benzyloxy)-1-(3-butenyl)-3-methoxybenzene (12.13 g, 45.2 mmol) in water:tert-butyl alcohol (1:1, 300 mL) and the reaction mixture was allowed to stir at room temperature for 12 h. The reaction mixture was quenched by the addition of sodium sulfite. The reaction mixture was diluted with water (500 mL) and ethyl acetate (500 mL). The aqueous phase was separated and extracted with ethyl acetate (2×200 mL). The combined organic extracts were washed with aqueous sodium chloride (400 mL), dried (magnesium sulfate) and the solvent was removed in vacuo to give a crude oil. Purification by flash column chromatography (silica, ethyl acetate:hexanes 4:1) gave 12.57 g (92%, 40% ee) of (2S)-4-[2-(benzyloxy)-3-methoxyphenyl]-1,2-butanediol as a colorless oil. $[\alpha]_D^{25}$=−3.04 (c 10.2 in methanol, 40% ee); $R_f$=0.72 (silica, ethyl acetate:hexanes 4:1); Anal. Calcd. for $C_{18}H_{22}O_4$.0.1 $H_2O$: C, 71.08; H, 7.36. Found: C, 70.95; H, 7.33.

Intermediate 3

[8-Methoxy-3,4-dihydro-2H-chromen-2-yl]methanol

To a solution of (2S)-4-[2-(benzyloxy)-3-methoxyphenyl]-1,2-butanediol (12.00 g, 39.7 mmol) in ethanol (400 mL) was added palladium on carbon (10 wt. %, 1.2 g) and the reaction mixture was shaken under an $H_2$ atmosphere (50 psi) for 12 h. The reaction mixture was filtered (celite) and the solvent removed in vacuo to provide a crude oil. The residue was dissolved in hydrogen bromide (30 wt. % in acetic acid, 100 mL) and the reaction mixture was stirred at 0° C. for 2 h. The reaction mixture was quenched by the addition of water (500 mL) and extracted with ethyl acetate (3×200 mL). The combined organic extracts were washed with water (3×200 mL), aqueous sodium chloride (300 mL), dried (magnesium sulfate), and the solvent was removed in vacuo to provide a crude oil. The residue was dissolved in methanol (100 mL) and the resulting solution was slowly added to a solution of aqueous sodium hydroxide (2.5 M, 150 mL) in water (350 mL) and the reaction mixture was allowed to stir at 0° C. for 30 min. The reaction mixture was quenched by the addition of aqueous hydrogen chloride (1.0 M, 500 mL) and was extracted with ethyl acetate (3×200 mL). The combined organic extracts were washed with water (2×200 mL), aqueous sodium chloride (300 mL), dried (magnesium sulfate), and the solvent was removed in vacuo to provide a crude oil. Purification by flash column chromatography (silica, ethyl acetate:hexanes 1:1) gave 5.38 g (70%, 40% ee) of [(2R)-8-methoxy-3,4-dihydro-2H-chromen-2-yl]methanol as a white crystalline solid. $[\alpha]_D^{25}$ –60.51 (c 9.62 in chloroform, 40% ee); $R_f$=0.52 (silica, ethyl acetate:hexanes 1:1); mp 65–69° C.; Anal. Calcd. for $C_{11}H_{14}O_3$: C, 68.02; H, 7.27. Found: C, 67.92; H, 7.30.

Intermediate 4

[8-Methoxy-3,4-dihydro-2H-chromen-2-ylmethyl 4-methylbenzenesulfonate

To a solution of [(2R)-8-methoxy-3,4-dihydro-2H-chromen-2-yl]methanol (5.00 g, 25.7 mmol) in dichloromethane (250 mL) was added p-toluenesulfonyl chloride (9.82 g, 51.5 mmol), 4-(dimethylamino)pyridine (0.62 g, 5.15 mmol), and N,N-diisopropylethylamine (8.32 g, 64.4 mmol) and the reaction mixture was heated to 50° C. for 12 h. The reaction mixture was quenched by the addition of water (500 mL). The aqueous layer was separated and extracted with dichloromethane (2×200 mL). The combined organic extracts were washed with aqueous hydrogen chloride (1.0 M, 200 mL), water (200 mL), aqueous sodium chloride (200 mL), dried (magnesium sulfate), and the solvent was removed in vacuo to provide a crude solid. Purification by flash column chromatography (silica, ethyl acetate:hexanes 2:3) gave 6.45 g (72%, 40% ee) of [(2R)-8-methoxy-3,4-dihydro-2H-chromen-2-yl]methyl 4-methylbenzenesulfonate as a white crystalline solid. $[\alpha]_D^{25}$=–20.30 (c 13.1 in chloroform, 40% ee); $R_f$=0.71 (silica, ethyl acetate:hexanes 2:3); mp 115–117° C.; Anal. Calcd. for $C_{18}H_{20}O_5S$: C, 62.05; H, 5.79. Found: C, 61.99; H, 5.81.

EXAMPLE 4

5-Fluoro-3-(1-{[8-methoxy-3,4-dihydro-2H-chromen-2-yl]methyl}-1,2,3,6-tetrahydro-4-pyridinyl)-1H-indole To a solution of [(2R)-8-methoxy-3,4-dihydro-2H-chromen-2-yl]methyl 4-methylbenzenesulfonate (0.348 g, 1.00 mmol) in methyl sulfoxide (20 mL) was added 5-fluoro-3-(1,2,3,6-tetrahydro-4-pyridinyl)-1H-indole (0.865 g, 4.00 mmol) and the reaction mixture was heated to 80° C. for 12 h. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, ethyl acetate:hexanes 4:1) followed by recrystallization from ethanol provided 0.271 g (69%, 40% ee) of 5-fluoro-3-(1-{[(2R)-8-methoxy-3,4-dihydro-2H-chromen-2-yl]methyl}-1,2,3,6-tetrahydro-4-pyridinyl)-1H-indole as a tan crystalline powder. $[\alpha]_D^{25}$=–22.05 (c 9.98 in chloroform, 40% ee); $R_f$=0.49 (silica, ethyl acetate:hexanes 4:1); mp 177–180° C. dec; Anal. Calcd. for $C_{24}H_{25}FN_2O_2$: C, 73.45; H, 6.42; N, 7.14. Found: C, 73.03; H, 6.49; N, 7.12.

EXAMPLE 5

(3-(1-{8-Methoxy-3,4-dihydro-2H-chromen-2-yl]methyl}-1,2,3,6-tetrahydro-4-pyridinyl)-1H-indole To a solution of [(2R)-8-methoxy-3,4-dihydro-2H-chromen-2-yl]methyl 4-methylbenzenesulfonate (0.348 g, 1.00 mmol) in methyl sulfoxide (20 mL) was added 3-(1,2,3,6-tetrahydro-4-pyridinyl)-1H-indole (0.793 g, 4.00 mmol) and the reaction mixture was heated to 80° C. for 12 h. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, ethyl acetate:hexanes 4:1) followed by recrystallization from ethanol provided 0.254 g (68%, 40% ee) of 3-(1-{[(2R)-8-methoxy-3,4-dihydro-2H-chromen-2-yl]methyl}-1,2,3,6-tetrahydro-4-pyridinyl)-1H-indole as a yellow crystalline powder. $[\alpha]_D^{25}$=–28.22 (c 9.92 in chloroform, 40% ee); $R_f$=0.34 (silica, ethyl acetate:hexanes 4:1); mp 190–194° C. dec; Anal. Calcd. for $C_{24}H_{26}N_2O_2 \cdot 0.1 H_2O$: C, 76.61; H, 7.02; N, 7.44. Found: C, 76.42; H, 6.99 N, 7.43.

EXAMPLE 6

3-[1-(3,4-Dihydro-2H-chromen-2-ylmethyl)-1 2,3,6-tetrahydro-4-pyridinyl]-6-fluoro-1H-indole To a solution of 3,4-dihydro-2H-chromen-2-ylmethyl 4-methylbenzenesulfonate (0.424 g, 1.33 mmol) in methyl sulfoxide (5 mL) was added 6-fluoro-3-(1,2,3,6-tetrahydro-4-pyridinyl)-1H-indole (0.300 g, 1.33 mmol) and the reaction mixture was heated to 80° C. for 12 h. The reaction mixture was allowed to cool to room temperature and was poured into 100 mL of saturated aqueous sodium bicarbonate and extracted twice with 100 mL portions of methylene chloride. The combined organic extracts were dried over sodium sulfate, filtered and concentrated in vacuo. The residue was column chromatographed on silica gel with 3% methanol in methylene chloride as eluant. Combination and evaporation of the product fractions gave 0.25 g (51%) of the product as a yellow oil. This was recrystallized from ethanol to give 0.13 g of 3-[1-(3,4-dihydro-2H-chromen-2-ylmethyl)-1,2,3,6-tetrahydro-4-pyridinyl]-6-fluoro-1H-indole as a white solid. mp 160–161° C.; Anal. Calcd. for $C_{23}H_{23}FN_2O$: C, 75.97; H, 7.77; N, 7.79. Found: C, 76.22; H, 6.40; N, 7.73.

EXAMPLE 7

6-Fluoro-3-(1-{[8-methoxy-3,4-dihydro-2H-chromen-2-yl]methyl}-1,2,3,6-tetrahydro-4-pyridinyl)-1H-indole To a solution of [(2R)-8-methoxy-3,4-dihydro-2H-chromen-2-yl]methyl 4-methylbenzenesulfonate (0.348 g, 1.00 mmol) in methyl sulfoxide (20 mL) was added 6-fluoro-3-(1,2,3,6-tetrahydro-4-pyridinyl)-1H-indole (0.865 g, 4.00 mmol) and the reaction mixture was heated to 80° C. for 12 h. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, ethyl acetate:hexanes 4:1) followed by recrystallization from ethanol provided 0.243 g (62%, 40% ee) of 6-fluoro-3-(1-{[(2R)-8-methoxy-3,4-dihydro-2H-chromen-2-yl]methyl}-1,2,3,6-tetrahydro-4-pyridinyl)-1H-indole as a tan crystalline powder. $[\alpha]_D^{25}$=–27.14 (c 9.95 in chloroform, 40% ee); $R_f$=0.47 (silica, ethyl acetate:hexanes 4:1); mp >170° C. dec; Anal. Calcd. for $C_{24}H_{25}FN_2O_2 \cdot 0.1 H_2O$: C, 73.11; H, 6.44; N, 7.11. Found: C, 72.81; H, 6.36; N, 7.06.

Intermediate 5

2-(2-Methoxy-6-vinylphenoxy)-3-butenyl 4-methylbenzenesulfonate

To a suspension of methyltriphenylphoshonium bromide (19.65 g, 55.00 mmol) in THF (200 mL) cooled to 0° C. was added n-butyllithium (1.6 M in hexanes, 37.5 mL, 60.00 mmol) and the reaction mixture was allowed to stir at 0° C. for 30 min. The ylide was added via cannula to a solution of 3-methoxysalicylaldehyde (3.80 g, 25.00 mmol) in THF (100 mL) and the reaction mixture was allowed to stir at room temperature for 3 h. The reaction mixture was quenched by the addition of aqueous ammonium chloride (100 mL) and diluted with water (300 mL). The aqueous layer was separated and extracted with diethyl ether (3×200 mL). The combined organic extracts were washed with water (300 mL), aqueous sodium chloride (300 mL), dried (magnesium sulfate) and filtered through a plug of silica (10 cm×5 cm). The solvent was removed in vacuo to give the 2-vinylphenol as a crude oil which was dissolved in tetrahydrofuran (200 mL). To the resulting solution of was added (S)-2-hydroxy-3-buten-1-yl p-tosylate (7.27 g, 30.00 mmol), triphenylphoshine (7.87 g, 30.00 mmol), and diethyl azodicarboxylate (5.22 g, 30.00 mmol). The reaction mixture was allowed to stir at room temperature for 12 h. The reaction mixture was quenched by the addition of water (200 mL). The aqueous layer was separated and extracted with ethyl acetate (2×250 mL). The combined organic extracts were washed with water (200 mL), aqueous sodium chloride (300 mL), dried (magnesium sulfate) and the solvent was removed in vacuo to give a crude solid. Purification by flash column chromatography (silica, ethyl acetate:hexanes 4:1) provided 5.33 g (57%, >97% ee) of (2R)-2-(2-methoxy-6-vinylphenoxy)-3-butenyl 4-methylbenzenesulfonate as a colorless oil. $[\alpha]_D^{25}$=−8.06 (c 9.93 in chloroform, >97% ee); $R_f$=0.57 (silica, ethyl acetate:hexanes 3:7); Anal. Calcd. for $C_{20}H_{22}O_5S \cdot 0.2\ H_2O$: C, 63.57; H, 5.97. Found: C, 63.37; H, 5.66.

Intermediate 6

[8-Methoxy-2H-chromen-2-yl]methyl 4-methyl benzenesulfonate

To a solution of (2R)-2-(2-methoxy-6-vinylphenoxy)-3-butenyl 4-methyl-benzenesulfonate (3.00 g, 8.01 mmol) in dichloromethane (100 mL) was added bis(tricyclopentylphoshine)benzylidene ruthenium(IV) dichloride (0.59 g, 0.80 mmol) and the reaction mixture was stirred at room temperature for 4 h. The solvent was removed in vacuo to give a crude solid. Purification by flash column chromatography (silica, ethyl acetate:hexanes 2:3) provided 2.47 g (68%, >97% ee) of [(2R)-8-methoxy-2H-chromen-2-yl]methyl 4-methylbenzenesulfonate as a light purple oil. $[\alpha]_D^{25}$=+150.31 (c 10.18 in chloroform, >97% ee); $R_f$=0.53 (silica, ethyl acetate:hexanes 2:3); Anal. Calcd. for $C_{18}H_{18}O_5S \cdot 0.2\ H_2O$: C, 61.77; H, 5.29. Found: C, 61.49; H, 5.00.

EXAMPLE 8

5-Fluoro-3-(1-{[8-methoxy-2H-chromen-2-yl]methyl}-1,2,3,6-tetrahydro-4-pyridinyl)-1H-indole To a solution of [(2R)-8-methoxy-2H-chromen-2-yl]methyl 4-methyl-benzenesulfonate (0.350 g, 1.01 mmol) in methyl sulfoxide (20 mL) was added 5-fluoro-3-(1,2,3,6-tetrahydro-4-pyridinyl)-1H-indole (0.655 g, 3.03 mmol) and the reaction mixture was heated to 80° C. for 12 h. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.240 g (61%, >97% ee) of 5-fluoro-3-(1-{[(2R)-8-methoxy-2H-chromen-2-yl]methyl}-1,2,3,6-tetrahydro-4-pyridinyl)-1H-indole as a yellow solid. $[\alpha]_D^{25}$=−2.14 (c 10.27 in chloroform, >97% ee); $R_f$=0.49 (silica, methanol:ethyl acetate 1:9); mp 189–191° C. dec; Anal. Calcd. for $C_{24}H_{23}FN_2O_2 \cdot 0.3\ H_2O$: C, 73.15; H, 5.99; N, 7.11. Found: C, 73.19; H, 6.03; N, 7.08.

EXAMPLE 9

3-(1-{[8-Methoxy-2H-chromen-2-yl]methyl}-1,2,3,6-tetrahydro-4-pyridinyl)-1H-indole To a solution of [(2R)-8-methoxy-2H-chromen-2-yl] methyl 4-methyl-benzenesulfonate (0.350 g, 1.01 mmol) in methyl sulfoxide (20 mL) was added 3-(1,2,3,6-tetrahydro-4-pyridinyl)-1H-indole (0.601 g, 3.03 mmol) and the reaction mixture was heated to 80° C. for 12 h. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.218 g (58%, >97% ee) of 3-(1-{[(2R)-8-methoxy-2H-chromen-2-yl]methyl}-1,2,3,6-tetrahydro-4-pyridinyl)-1H-indole as a yellow solid. $[\alpha]_D^{25}$=+0.588 (c 10.21 in chloroform, >97% ee); $R_f$=0.43 (silica, methanol:ethyl acetate 1:9); mp 198–200° C. dec; Anal. Calcd. for $C_{24}H_{24}N_2O_2 \cdot 0.3\ H_2O$: C, 76.29; H, 6.56; N, 7.41. Found: C, 76.02; H, 6.63; N, 7.43.

Intermediate 7

2-((3S)-4-{[tert-butyl(dimethyl)silyl]oxy}-3-hydroxybutyl)-6-methoxyphenol

To a solution of (2S)-4-[2-(benzyloxy)-3-methoxyphenyl]-1,2-butanediol (8.00 g, 26.5 mmol) in N,N-dimethylformamide (250 mL) cooled to 0° C. was added tert-butyldimethylsilyl chloride (4.39 g, 29.1 mmol) followed by imidazole (2.16 g, 31.8 mmol) and the reaction mixture was allowed to stir at room temperature for 4 h. The reaction mixture was diluted with water (500 mL) and ethyl acetate (200 mL). The aqueous phase was separated and extracted with ethyl acetate (2×100 mL). The combined organic extracts were washed with aqueous hydrogen chloride (200 mL), water (4×200 mL), aqueous sodium chloride (300 mL), dried (magnesium sulfate) and the solvent was removed in vacuo to give a crude oil. The residue was dissolved in ethanol (300 mL), palladium on carbon (10 wt. %, 1.00 g) was added, and the reaction mixture was shaken under an $H_2$ atmosphere (50 psi) for 6 h. The reaction mixture was filtered (celite) and the solvent removed in vacuo to provide a crude oil. Purification by flash column chromatography (silica, ethyl acetate:hexanes 1:4) gave 7.33 g (85%, 40% ee) of 2-((3S)-4-{[tert-butyl(dimethyl)silyl]oxy}-3-hydroxybutyl)-6-methoxyphenol as a colorless oil which crystallized upon standing. $R_f$=0.53 (silica, ethyl acetate:hexanes 1:4); mp 44–46° C.; Anal. Calcd. for $C_{17}H_{30}O_4Si$: C, 62.54; H, 9.26. Found: C, 62.41; H, 9.19.

Intermediate 8 tert-butyl(dimethyl)silyl [(2R)-8-methoxy-3,4-dihydro-2H-chromen-2-yl]methyl Ether To a solution of 2-((3S)-4-{[tert-butyl(dimethyl)silyl]oxy}-3-hydroxybutyl)-6-methoxyphenol (6.90 g, 21.1 mmol) in toluene (250 mL) cooled to 0° C. was added triphenylphoshine (6.10 g, 23.2 mmol) followed by dropwise addition of diethyl azodicarboxylate (4.05 g, 23.2 mmol). The reaction mixture was allowed to stir at room temperature for 15 min. The reaction mixture was quenched by the addition of water (300 mL). The aqueous layer was separated and extracted with diethyl ether (2×150 mL). The combined organic extracts were washed with water (200 mL), aqueous sodium chloride (300 mL), dried (magnesium sulfate) and the solvent was removed in vacuo to give a crude oil. Purification by flash column chromatography (silica, ethyl acetate:hexanes 1:4) provided 4.94 g (76%, 40% ee) of tert-butyl(dimethyl)silyl [(2R)-8-methoxy-3,4-dihydro-2H-chromen-2-yl]methyl ether as a colorless oil. $[\alpha]_D^{25}$=−25.84 (c 10.82 in chloroform, 40% ee); $R_f$=0.68 (silica, ethyl acetate:hexanes 1:4); Anal. Calcd. for $C_{17}H_{28}O_3Si \cdot 0.1 H_2O$: C, 65.8; H, 9.16. Found: C, 65.75; H, 8.88.

Intermediate 9

[(2R)-8-methoxy-3,4-dihydro-2H-chromen-2-yl] methanol

Method A: from (2S)-4-[2-(benzyloxy)-3-methoxyphenyl]-1,2-butanediol

To a solution of (2S)-4-[2-(benzyloxy)-3-methoxyphenyl]-1,2-butanediol (12.00 g, 39.7 mmol) in ethanol (400 mL) was added palladium on carbon (10 wt. %, 1.2 g) and the reaction mixture was shaken under an $H_2$ atmosphere (50 psi) for 12 h. The reaction mixture was filtered (celite) and the solvent removed in vacuo to provide a crude oil. The residue was dissolved in hydrogen bromide (30 wt. % in acetic acid, 200 mL) and the reaction mixture was stirred at 0° C. for 2 h. The reaction mixture was quenched by the addition of water (500 mL) and extracted with ethyl acetate (3×200 mL). The combined organic extracts were washed with water (3×200 mL), aqueous sodium chloride (300 mL), dried (magnesium sulfate), and the solvent was removed in vacuo to provide a crude oil. The residue was dissolved in methanol (100 mL) and the resulting solution was slowly added to a solution of aqueous sodium hydroxide (2.5 M, 150 mL) in water (350 mL) and the reaction mixture was allowed to stir at 0° C. for 30 min. The reaction mixture was quenched by the addition of aqueous hydrogen chloride (1.0 M, 500 mL) and extracted with ethyl acetate (3×200 mL). The combined organic extracts were washed with water (2×200 mL), aqueous sodium chloride (300 mL), dried (magnesium sulfate), and the solvent was removed in vacuo to provide a crude oil. Purification by flash column chromatography (silica, ethyl acetate:hexanes 1:1) gave 5.38 g (70%, 40% ee) of [(2R)-8-methoxy-3,4-dihydro-2H-chromen-2-yl]methanol as a white crystalline solid. $[\alpha]_D^{25}$=−60.51 (c 9.62 in chloroform, 40% ee); $R_f$=0.52 (silica, ethyl acetate:hexanes 1:1); mp 65–69° C.; Anal. Calcd. for $C_{11}H_{14}O_3$: C, 68.02; H, 7.27. Found: C, 67.92; H, 7.30.

Method B: from tert-butyl(dimethyl)silyl [(2R)-8-methoxy-3,4-dihydro-2H-chromen-2-yl]methyl Ether To a solution of tert-butyl(dimethyl)silyl [(2R)-8-methoxy-3,4-dihydro-2H-chromen-2-yl]methyl ether (4.50 g, 14.6 mmol) in tetrahydrofuran (150 mL) at 0° C. was added excess tetrabutylammonium fluoride (1.0 M in tetrahydrofuran) and the reaction mixture was allowed to stir at 22° C. for 30 min. The solvent was removed in vacuo and the residue was purified by flash column chromatography (silica, ethyl acetate:hexanes 1:1) to give 2.49 g (88%, 40% ee) of [(2R)-8-methoxy-3,4-dihydro-2H-chromen-2-yl] methanol as a white crystalline solid.

Intermediate 10

[(2R)-8-methoxy-3,4-dihydro-2H-chromen-2-yl] methyl 4-methylbenzenesulfonate

To a solution of [(2R)-8-methoxy-3,4-dihydro-2H-chromen-2-yl]methanol (5.00 g, 25.7 mmol) in dichloromethane (250 mL) was added p-toluenesulfonyl chloride (9.82 g, 51.5 mmol), 4-(dimethylamino)pyridine (0.62 g, 5.15 mmol), and N,N-diisopropylethylamine (8.32 g, 64.4 mmol) and the reaction mixture was heated to 50° C. for 12 h. The reaction mixture was quenched by the addition of water (500 mL). The aqueous layer was separated and extracted with dichloromethane (200 mL). The combined organic extracts were washed with aqueous hydrogen chloride (1.0 M, 200 mL), water (200 mL), aqueous sodium chloride (200 mL), dried (magnesium sulfate), and the solvent was removed in vacuo to provide a crude solid. Purification by flash column chromatography (silica, ethyl acetate:hexanes 2:3) gave 6.45 g (72%, 40% ee) of [(2R)-8-methoxy-3,4-dihydro-2H-chromen-2-yl]methyl 4-methylbenzenesulfonate as a white crystalline solid. $[\alpha]_D^{25}$=−20.30 (c 13.1 in chloroform, 40% ee); $R_f$=0.71 (silica, ethyl acetate:hexanes 2:3); mp 115–117° C.; Anal. Calcd. for $C_{18}H_{20}O_5S$: C, 62.05; H, 5.79. Found: C, 61.99; H, 5.81.

Intermediate 11

[1-(benzyloxy)-2-naphthyl]methanol

To a solution of 1-(benzyloxy)-2-naphthaldehyde (7.00 g, 26.7 mmol) in methanol (250 mL) at 0° C. was added sodium borohydride (1.51 g, 40.0 mmol) and the reaction mixture was allowed to stir at room temperature for 24 h. The solvent was removed in vacuo to give a crude solid which was partitioned between ethyl acetate (300 mL) and water (300 mL). The organic layer was separated and washed with water (300 mL), aqueous sodium chloride (300 mL), dried (magnesium sulfate) and filtered through a plug of silica (10 cm×5 cm). The solvent was removed in vacuo to give 6.98 g (99%) of [1-(benzyloxy)-2-naphthyl]methanol as white crystalline solid. $R_f$=0.36 (silica, dichloromethane:hexanes 3:2); mp 85–87° C. Anal. Calcd. for $C_{18}H_{16}O_2$: C, 81.24; H, 6.14. Found: C, 81.03; H, 5.98.

Intermediate 12

(2S)-4-[1-(benzyloxy)-2-naphthyl]-1,2-butanediol

To a solution of [1-(benzyloxy)-2-naphthyl]methanol (7.22 g, 27.3 mmol) in dichloromethane (300 mL) at 0° C. was added carbon tetrabromide (9.95 g, 30.0 mmol) followed by portionwise addition of triphenyl phosphine (7.52 g, 28.7 mmol) and the reaction mixture was allowed to stir for 15 min. The reaction was quenched by the addition of water (300 mL) and extracted with dichloromethane (200 mL). The combined organic layers were washed with water (200 mL), aqueous sodium chloride (200 mL), dried (magnesium sulfate) and the solvent was removed in vacuo to give a crude solid. Purification by flash column chromatography (silica, ethyl acetate:hexanes 1:9) gave 8.57 g (96%) of a colorless oil which was dissolved in tetrahydrofuran (300 mL). The solution was cooled to 0° C. and allyl magnesiumbromide (1.0 M in diethyl ether, 39.3 mL, 39.3 mmol) was added dropwise and the reaction mixture was allowed to stir for 12 h at room temperature. The reaction was quenched by the addition of aqueous ammonium chloride (100 mL) and water (200 mL) and extracted with diethyl ether (2×150 mL). The combined organic layers extracts were washed with water (400 mL), aqueous sodium chloride (200 mL), dried (magnesium sulfate) and the solvent was removed in vacuo to give an oil. Purification by flash column chromatography (silica, ethyl acetate:hexanes 1:20) gave 5.74 g (76%) of a colorless oil which was dissolved in water:tert-butyl alcohol (1:1, 100 mL) and added via an addition funnel to a suspension of AD-mix α (27.87 g) in water:tert-butyl alcohol (1:1, 200 mL) and the reaction mixture was allowed to stir at 0° C. for 12 h. The reaction mixture was quenched by the addition of sodium sulfite. The reaction mixture was diluted with water (300 mL) and ethyl acetate (200 mL). The aqueous phase was separated and extracted with ethyl acetate (2×150 mL). The combined organic extracts were washed with aqueous sodium chloride (250 mL), dried (magnesium sulfate) and the solvent was removed in vacuo to give a crude oil. Purification by flash column chromatography (silica, ethyl acetate:hexanes 4:1) gave 5.39 g (84%, 50% ee) of (2S)-4-[1-(benzyloxy)-2-naphthyl]-1,2-butanediol as a colorless oil. $[\alpha]_D^{25}$=−3.94 (c 19.31 in methanol, 50% ee); $R_f$=0.56 (silica, ethyl acetate:hexanes 4:1); Anal. Calcd. for $C_{21}H_{22}O_3 \cdot 0.25$ $CH_3CO_2C_2H_5$C, 76.72; H, 7.02. Found: C, 76.31; H, 7.00.

Intermediate 13

(2S)-4-(1-hydroxy-2-naphthyl)-1,2-butanediol

To a solution of (2S)-4-[1-(benzyloxy)-2-naphthyl]-1,2-butanediol (5.63 g, 17.5 mmol) in ethanol (150 mL), palladium on carbon (10 wt. %, 0.56 g) was added, and the reaction mixture was shaken under an $H_2$ atmosphere (50 psi) for 6 h. The reaction mixture was filtered (celite) and the solvent removed in vacuo to provide a crude oil. Purification by flash column chromatography (silica, ethyl acetate:hexanes 4:1) gave 3.81 g (94%, 50% ee) of (2S)-4-(1-hydroxy-2-naphthyl)-1,2-butanediol as a colorless oil which crystallizes upon standing. $[\alpha]_D^{25}$=+11.93 (c 10.06 in chloroform, 50% ee); $R_f$=0.50 (silica, ethyl acetate:hexanes 4:1); mp 105–108° C.; Anal. Calcd. for $C_{14}H_{16}O_3$: C, 72.39; H, 6.94. Found: C, 72.20; H, 7.18.

Intermediate 14

(2R)-3,4-dihydro-2H-benzo[h]chromen-2-ylmethanol (2S)-4-(1-hydroxy-2-naphthyl)-1,2-butanediol (3.50 g, 15.1 mmol) was dissolved in hydrogen bromide (30 wt. % in acetic acid, 100 mL) and the reaction mixture was stirred at 0° C. for 2 h. The reaction mixture was quenched by the addition of water (500 mL) and extracted with ethyl acetate (3×200 mL). The combined organic extracts were washed with water (3×200 mL), aqueous sodium chloride (300 mL), dried (magnesium sulfate), and the solvent was removed in vacuo to provide a crude oil. The residue was dissolved in methanol (100 mL) and the resulting solution was slowly added to a solution of aqueous sodium hydroxide (2.5 M, 150 mL) in water (350 mL) and the reaction mixture was allowed to stir at 0° C. for 30 min. The reaction mixture was quenched by the addition of aqueous hydrogen chloride (1.0 M, 500 mL) and extracted with ethyl acetate (3×200 mL). The combined organic extracts were washed with water (2×200 mL), aqueous sodium chloride (300 mL), dried (magnesium sulfate) and the solvent was removed in vacuo to provide a crude oil. Purification by flash column chromatography (silica, ethyl acetate:hexanes 1:1) gave 5.38 g (70%, 50% ee) of (2R)-3,4-dihydro-2H-benzo[h]chromen-2-ylmethanol as a colorless oil. $[\alpha]_D^{25}$=−51.23 (c 11.58 in chloroform, 50% ee); $R_f$=0.52 (silica, ethyl acetate:hexanes 1:1); Anal. Calcd. for $C_{14}H_{14}O_2 \cdot 0.25$ $H_2O$: C, 76.86; H, 6.68. Found: C, 76.47; H, 6.38.

Intermediate 15

(2R)-3,4-dihydro-2H-benzo[h]chromen-2-ylmethyl 4-methylbenzenesulfonate

To a solution of (2R)-3,4-dihydro-2H-benzo[h]chromen-2-ylmethanol (0.90 g, 4.22 mmol) in dichloromethane (50 mL) was added p-toluenesulfonyl chloride (1.61 g, 8.44 mmol), 4-(dimethylamino)pyridine (0.10 g, 0.84 mmol), and N,N-diisopropylethylamine (1.20 g, 9.28 mmol) and the reaction mixture was heated to 50° C. for 12 h. The reaction mixture was quenched by the addition of water (100 mL). The aqueous layer was separated and extracted with dichloromethane (100 mL). The combined organic extracts were washed with aqueous hydrogen chloride (1.0 M, 100 mL), water (100 mL), aqueous sodium chloride (100 mL), dried (magnesium sulfate), and the solvent was removed in vacuo to provide a crude solid. Purification by flash column chromatography (silica, ethyl acetate:hexanes 2:3) gave 1.20 g (77%, 50% ee) of (2R)-3,4-dihydro-2H-benzo[h]chromen-2-ylmethyl 4-methylbenzenesulfonate as a white solid. $[\alpha]_D^{25}$=−10.23 (c 10.16 in chloroform, 50% ee); $R_f$=0.68 (silica, ethyl acetate:hexanes 2:3); mp 107–111° C.; Anal. Calcd. for $C_{21}H_{20}O_4S$: C, 68.46; H, 5.47. Found: C, 68.10; H, 5.27.

Intermediate 16

(2R)-2-{2-[1-propenyl]phenoxy}-3-butenyl 4-methylbenzenesulfonate

To a solution of 2-[1-propenyl]phenol (3.00 g, 22.4 mmol) in toluene (200 mL) cooled to 0° C. was added (S)-2-hydroxy-3-buten-1-yl p-tosylate (8.12 g, 33.5 mmol) and triphenylphoshine (9.24 g, 35.2 mmol), followed by dropwise addition of diethyl azodicarboxylate (6.13 g, 35.2 mmol), and the reaction mixture was allowed to stir at room temperature for 12 h. The reaction mixture was quenched by the addition of water (200 mL). The aqueous layer was separated and extracted with diethyl ether (2×200 mL). The combined organic extracts were washed with water (200 mL), aqueous sodium chloride (300 mL), dried (magnesium sulfate) and the solvent was removed in vacuo to give a crude solid. Purification by flash column chromatography (silica, ethyl acetate:hexanes 3:7) provided 5.17 g (64%, >97% ee) of (2R)-2-{2-[1-propenyl]phenoxy}-3-butenyl 4-methylbenzenesulfonate as a colorless oil. $[\alpha]_D^{25}$=−15.0 (c 6.6 in methanol, >97% ee); $R_f$=0.47 (silica, ethyl acetate:hexanes 3:7); Anal. Calcd. for $C_{20}H_{22}O_4S$: C, 67.02; H, 6.19. Found: C, 67.56; H, 6.25.

Intermediate 17

(2R)-2H-chromen-2-ylmethyl 4-methylbenzenesulfonate

To a solution of (2R)-2-{2-[1-propenyl]phenoxy}-3-butenyl 4-methyl-benzenesulfonate (3.61 g, 10.1 mmol) in dichloromethane (100 mL) was added bis(tricyclopentylphoshine)benzylidene ruthenium(IV) dichloride (1.49 g, 2.01 mmol) and the reaction mixture was stirred at room temperature for 16 h. The solvent was removed in vacuo to give a crude solid. Purification by flash column chromatography (silica, ethyl acetate:hexanes 3:7) provided 2.48 g (78%, >97% ee) of (2R)-2H-chromen-2-ylmethyl 4-methylbenzenesulfonate as a pale green crystalline solid. $[\alpha]_D^{25}$=+175.12 (c 9.99 in methanol, >97% ee); $R_f$=0.40 (silica, ethyl acetate:hexanes 3:7); Anal. Calcd. for $C_{11}H_{16}O_4S$: C, 64.54; H, 5.10. Found: C, 64.85; H, 5.05.

Intermediate 18

(2R)-3,4-dihydro-2H-chromen-2-ylmethyl 4-methylbenzenesulfonate

To a solution of (2R)-2H-chromen-2-ylmethyl 4-methylbenzenesulfonate (1.70 g, 55.00 mmol) in ethanol (100 mL) was added palladium on carbon (10 wt. %, 0.17 g) and the reaction mixture was shaken under an $H_2$ atmosphere (50 psi) for 6 h. The reaction mixture was filtered (celite) and the solvent removed in vacuo to provide (2R)-3,4-dihydro-2H-chromen-2-ylmethyl 4-methylbenzenesulfonate (1.62 g, 95%) as a colorless oil which crystallized upon standing. $[\alpha]_D^{25}$=−52.69 (c 10.06 in methanol, >97% ee); $R_f$=0.60 (silica, ethyl acetate:hexanes 2:3); Anal. Calcd. for $C_{17}H_{18}O_4S$: C, 64.13; H, 5.70. Found: C, 63.90; H, 5.71.

Intermediate 19

(2R)-2-(2-methoxy-6-vinylphenoxy)-3-butenyl 4-methylbenzenesulfonate

To a suspension of methyltriphenylphoshonium bromide (19.65 g, 55.00 mmol) in THF (200 mL) cooled to 0° C. was added n-butyllithium (1.6 M in hexanes, 37.5 mL, 60.00 mmol) and the reaction mixture was allowed to stir at 0° C. for 30 min. The ylide was added via cannula to a solution of 3-methoxysalicylaldehyde (3.80 g, 25.00 mmol) in THF (100 mL) and the reaction mixture was allowed to stir at room temperature for 3 h. The reaction mixture was quenched by the addition of aqueous ammonium chloride (100 mL) and diluted with water (300 mL). The aqueous layer was separated and extracted with diethyl ether (3×200 mL). The combined organic extracts were washed with water (300 mL), aqueous sodium chloride (300 mL), dried (magnesium sulfate) and filtered through a plug of silica (10 cm×5 cm). The solvent was removed in vacuo to give the 2-vinylphenol as a crude oil which was dissolved in tetrahydrofuran (200 mL). To the resulting solution of was added (S)-2-hydroxy-3-buten-1-yl p-tosylate (7.27 g, 30.00 mmol), triphenylphoshine (7.87 g, 30.00 mmol), and diethyl azodicarboxylate (5.22 g, 30.00 mmol). The reaction mixture was allowed to stir at room temperature for 12 h. The reaction mixture was quenched by the addition of water (200 mL). The aqueous layer was separated and extracted with ethyl acetate (2×250 mL). The combined organic extracts were washed with water (200 mL), aqueous sodium chloride (300 mL), dried (magnesium sulfate) and the solvent was removed in vacuo to give a crude solid. Purification by flash column chromatography (silica, ethyl acetate:hexanes 4:1) provided 5.33 g (57%, >97% ee) of (2R)-2-(2-methoxy-6-vinylphenoxy)-3-butenyl 4-methylbenzenesulfonate as a colorless oil. $[\alpha]_D^{25}$=−8.06 (c 9.93 in chloroform, >97% ee); $R_f$=0.57 (silica, ethyl acetate:hexanes 3:7); Anal. Calcd. for $C_{20}H_{22}O_5S.0.2 H_2O$: C, 63.57; H, 5.97. Found: C, 63.37; H, 5.66.

Intermediate 20

[(2R)-8-methoxy-2H-chromen-2-yl]methyl 4-methylbenzenesulfonate

To a solution of (2R)-2-(2-methoxy-6-vinylphenoxy)-3-butenyl 4-methyl-benzenesulfonate (3.00 g, 8.01 mmol) in dichloromethane (100 mL) was added bis(tricyclopentylphoshine)benzylidene ruthenium(IV) dichloride (0.59 g, 0.80 mmol) and the reaction mixture was stirred at room temperature for 4 h. The solvent was removed in vacuo to give a crude solid. Purification by flash column chromatography (silica, ethyl acetate:hexanes 2:3) provided 2.47 g (68%, >97% ee) of [(2R)-8-methoxy-2H-chromen-2-yl]methyl 4-methylbenzenesulfonate as a light purple oil. $[\alpha]_D^{5}$=+150.31 (c 10.18 in chloroform, >97% ee); $R_f$=0.53 (silica, ethyl acetate:hexanes 2:3); Anal. Calcd. for $C_{18}H_{18}O_5S.0.2 H_2O$: C, 61.77; H, 5.29. Found: C, 61.49; H, 5.00.

What is claimed is:

1. A compound of formula I

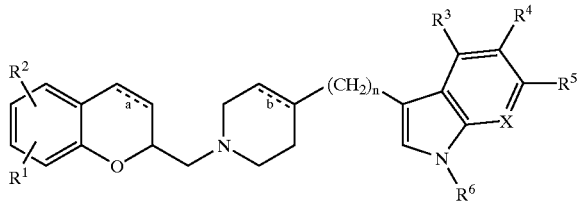

wherein $R^1$ and $R^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halo, cyano, carboxamido, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

the dotted lines at a and b independently represent optional double bonds; and n is an integer 0, 1 or 2;

or a pharmaceutically acceptable salt thereof.

2. A compound of claim 1 in which $R^1$ and $R^2$ are, independently, hydrogen, halo, cyano, carboxamido, trifluoromethyl, amino, alkyl of one to six carbon atoms or alkoxy of one to six carbon atoms.

3. A compound of claim 1 wherein $R^1$ is alkoxy of 1 to 6 carbon atoms.

4. A compound of claim 1 wherein $R^1$ and $R^2$, taken together form methylenedioxy, ethylenedioxy or propylenedioxy.

5. A compound of claim 1 in which $R^1$ is attached to position 8 of a chroman moiety.

6. A compound of claim 1 in which $R^3$, $R^4$, $R^5$ and $R^7$ are independently selected from hydrogen, halo, cyano, alkyl of one to six carbon atoms, or alkoxy of one to six carbon atoms.

7. A compound of claim 1 wherein $R^3$, $R^4$, $R^5$ and $R^7$ are independently selected from hydrogen, halogen or cyano.

8. A compound of claim 1 wherein $R^6$ is hydrogen or alkyl of 1 to 3 carbon atoms.

9. A compound of claim 1 wherein X is $CR^7$.

10. A compound according to claim 1 wherein $R^7$ is hydrogen, halogen or cyano.

11. A compound of claim 1 wherein n is 0 or 1.

12. A compound of claim 1 wherein the dotted line in the azaheterocycle represents a double bond.

13. A compound of claim 1 in which $R^1$ and $R^2$ are, independently, hydrogen, halo, cyano, carboxamido, trifluoromethyl, amino, alkyl of one to six carbon atoms or alkoxy of one to six carbon atoms; $R^3$, $R^4$, $R^5$ and $R^7$ are independently selected from hydrogen, halo, cyano, alkyl of one to six carbon atoms, or alkoxy of one to six carbon atoms; n is an integer 0 or 1; or a pharmaceutically acceptable salt thereof.

14. A compound of claim 1 in which $R^1$ is alkoxy of one to six carbon atoms and is attached to position 8 of a chroman moiety, $R^2$ and $R^4$ are hydrogen, $R^3$, $R^5$ and $R^7$ are independently selected from hydrogen, halo or cyano, X is $CR^7$, n is 0 and the dotted line in the azaheterocycle represents a double bond; or a pharmaceutically acceptable salt thereof.

15. The compound of claim 1 which is 2-{[1-(3,4-dihydro-2H-chromen-2-ylmethyl)-4-piperidinyl]methyl}-5-fluoro-1H-indole or a pharmaceutically acceptable salt thereof.

16. The compound of claim 1 which is 3-[1-(3,4-dihydro-2H-chromen-2-ylmethyl)-1,2,3,6-tetrahydro-4-pyridinyl]-1H-indole or a pharmaceutically acceptable salt thereof.

17. The compound of claim 1 which is 3-[1-(3,4-dihydro-2H-chromen-2-ylmethyl)-1,2,3,6-tetrahydro-4-pyridinyl]-5-fluoro-1H-indole or a pharmaceutically acceptable salt thereof.

18. The compound of claim 1 which is 5-fluoro-3-(1-{[8-methoxy-3,4-dihydro-2H-chromen-2-yl]methyl}-1,2,3,6-tetrahydro-4-pyridinyl)-1H-indole or a pharmaceutically acceptable salt thereof.

19. The compound of claim 1 which is (3-(1-{[8-methoxy-3,4-dihydro-2H-chromen-2-yl]methyl}-1,2,3,6-tetrahydro-4-pyridinyl)-1H-indole or a pharmaceutically acceptable salt thereof.

20. The compound of claim 1 which is 3-[1-(3,4-dihydro-2H-chromen-2-ylmethyl)-1,2,3,6-tetrahydro-4-pyridinyl]-6-fluoro-1H-indole or a pharmaceutically acceptable salt thereof.

21. The compound of claim 1 which is 6-fluoro-3-(1-{[8-methoxy-3,4-dihydro-2H-chromen-2-yl]methyl}-1,2,3,6-tetrahydro-4-pyridinyl)-1H-indole or a pharmaceutically acceptable salt thereof.

22. The compound of claim 1 which is 5-fluoro-3-(1-{[8-methoxy-2H-chromen-2-yl]methyl}-1,2,3,6-tetrahydro-4-pyridinyl)-1H-indole or a pharmaceutically acceptable salt thereof.

23. The compound of claim 1 which is 3-(1-{[8-methoxy-2H-chromen-2-yl]methyl}-1,2,3,6-tetrahydro-4-pyridinyl)-1H-indole or a pharmaceutically acceptable salt thereof.

24. A method of treating a subject suffering from a condition requiring SSR inhibition selected from the group consisting of depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders such as anorexia nervosa, bulimia nervosa, vasomotor flushing, cocaine and alcohol addiction, and sexual dysfunction, which comprises providing to the subject suffering from said condition, a SSR inhibitory effective amount of a compound of formula I

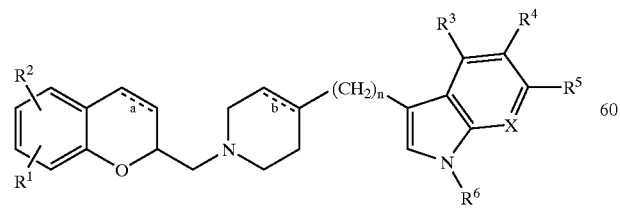

I wherein $R^1$ and $R^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halo, cyano, carboxamido, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

the dotted lines at a and b independently represent optional double bonds; and n is an integer 0, 1 or 2;

or a pharmaceutically acceptable salt thereof.

25. A method of claim 18 wherein the condition is depression.

26. The method of claim 18 wherein the condition is obsessive compulsive disorder, panic attacks, generalized anxiety disorder or social anxiety disorder.

27. A pharmaceutical composition comprising a therapeutically effective amount of a compound of formula I

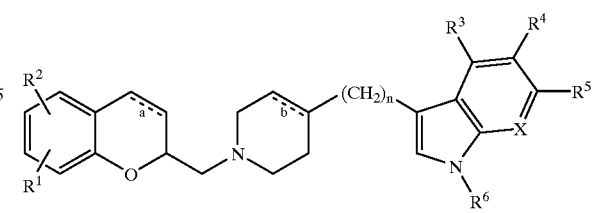

I wherein $R^1$ and $R^2$ are, independently, hydrogen, halo, cyano, carboxamido, carboalkoxy of two to six carbon atoms, trifluoromethyl, alkyl of 1 to 6 carbon atoms, alkoxy of, 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or $R^1$ and $R^2$, taken together, form methylenedioxy, ethylenedioxy or propylenedioxy;

$R^3$, $R^4$, $R^5$ and $R^7$ are independently selected from hydrogen, halo, cyano, carboxamido, trifluoromethyl, alkyl of 1 to 6 carbon atoms, alkoxy of 1 to 6 carbon atoms, alkanoyloxy of 2 to 6 carbon atoms;

$R^6$ is hydrogen or alkyl of 1 to 6 carbon atoms;

X is $CR^7$ or N;

the dotted lines at a and b independently represent optional double bonds; and n is an integer 0, 1 or 2;

or a pharmaceutically acceptable salt thereof, and a pharmaceutically acceptable carrier or excipient.

* * * * *